(12) United States Patent
Thomson et al.

(10) Patent No.: US 6,242,115 B1
(45) Date of Patent: *Jun. 5, 2001

(54) OLEDS CONTAINING THERMALLY STABLE ASYMMETRIC CHARGE CARRIER MATERIALS

(75) Inventors: Mark E. Thomson, Anaheim Hills; Bryan E. Koene, South Pasadena; Douglas E. Loy, Lakewood, all of CA (US)

(73) Assignee: The University of Southern California, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/925,029

(22) Filed: Sep. 8, 1997

(51) Int. Cl.$^7$ ................................................. H05B 33/12
(52) U.S. Cl. ...................... 428/690; 428/917; 428/411.1; 313/504; 313/506; 257/94
(58) Field of Search .................................. 428/690, 917, 428/411.1; 313/504, 506; 257/40, 94, 96; 564/308, 309, 426; 427/64, 66

(56) References Cited

U.S. PATENT DOCUMENTS

| | | | |
|---|---|---|---|
| 5,061,569 | 10/1991 | VanSlyke et al. | 428/457 |
| 5,281,489 | * 1/1994 | Mori et al. | 428/690 |
| 5,378,519 | * 1/1995 | Kikuchi et al. | 428/690 |
| 5,512,400 | * 4/1996 | Takesue et al. | 430/78 |
| 5,702,833 | * 12/1997 | Nagai et al. | 428/690 |
| 5,747,205 | * 5/1998 | Hu et al. | 430/59 |
| 5,792,557 | * 8/1998 | Nakaya et al. | 428/411.1 |
| 5,792,567 | * 8/1998 | Kido et al. | 428/690 |
| 5,811,833 | 9/1998 | Thompson | 257/40 |
| 5,968,675 | * 10/1999 | Tamano et al. | 428/690 |

FOREIGN PATENT DOCUMENTS 4-288369 * 10/1992 (JP).

OTHER PUBLICATIONS

K. Naito and A. Miura, J. Phys. Chem., vol. 97 (1993), pp. 6240–6248, (no month).

S. Tokito, H. Tanaka, A. Okada and Y. Taga, Appl. Phys. Lett., vol. 69, No. 7 (Aug. 1996), pp. 878–880.

Y. Shirota, T. Kobata and N. Noma, Chem. Lett. (1989), pp. 1145–1148, (no month).

T. Noda, I. Imae, N. Noma and Y. Shirota, Advance Materials, vol. 9, No. 3, (1997), pp. 239–241, (no month).

E. Han, L. Do, M. Fujihara, H. Inada and Y. Shirota, J. Appl. Phys., vol. 80 (Sep. 1996), pp. 3297–3305.

T. Noda, H. Ogawa, N. Noma Y. Shirota, Appl. Phys. Lett., vol. 70, No. 6, (Feb. 1997), pp. 699–701.

S. Van Slyke, C. Chen and C. Tang, Appl. Phys. Lett., vol. 69, No. 15 (Oct. 1996), pp. 2160–2162.

* cited by examiner

Primary Examiner—Marie Yamnitzky
(74) Attorney, Agent, or Firm—Kenyon & Kenyon

(57) ABSTRACT

Organic light emitting devices are comprised of an organic charge carrier layer formed from a charge carrier material that is capable of forming a stable glass due to the presence of a compound having an asymmetric molecular structure in the charge carrier material. For example, the OLED may contain hole transporting layers comprised of compounds having an asymmetric molecular structure in which hole transporting substituents are asymmetrically located around a core atom or core chemical group. The core atom may be a nitrogen atom or the core chemical group may be comprised of a single phenylene group or a biphenylene group which is substituted with at least two hole transporting amine groups, wherein at least one of the amine groups is different from at least one other amine group. For example, the compound may have the asymmetric molecular structure as shown by formula I:

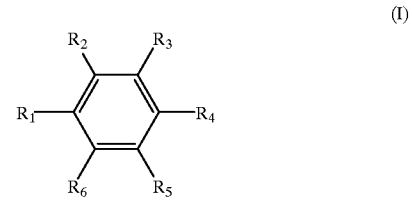

(I)

wherein $R_1$, $R_2$, $R_3$, $R_4$, $R_5$ and $R_6$ are, independently of one another, hole transporting amine groups, or hydrogen, with the proviso that at least two amine groups are present and at least one of the amine groups is different from at least one other amine group. Typically, $R_1$ and $R_4$ are hole transporting amine groups wherein $R_1$ is different from $R_4$.

13 Claims, 9 Drawing Sheets

OLEDS CONTAINING THERMALLY STABLE ASYMMETRIC CHARGE CARRIER MATERIALS

GOVERNMENT RIGHTS

This invention was made with Government support under Contract No. F33615-94-1-1414 awarded by DARPA. The government has certain rights in this invention.

FIELD OF INVENTION

The present invention is directed to organic light emitting devices (OLEDs) comprised of glassy charge carrier materials comprised of compounds having an asymmetric molecular structure, for example, hole transporting materials comprised of thermally stable asymmetric derivatives of phenyl or biphenyl diamines.

BACKGROUND OF THE INVENTION

Organic light emitting devices (OLEDs) are comprised of several organic layers in which one of the layers is comprised of an organic material that can be made to electroluminesce by applying a voltage across the device, C. W. Tang et al., *Appl. Phys. Lett* 51, 913 (1987). Certain OLEDs have been shown to have sufficient brightness, range of color and operating lifetimes for use as a practical alternative technology to LCD-based full color flat-panel displays (S. R. Forrest, P. E. Burrows and M. E. Thompson, Laser Focus World, Feb. 1995). Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor.

A transparent OLED (TOLED), which represents a significant step toward realizing high resolution, independently addressable stacked R-G-B pixels, was reported in International Patent Application No. PCT/US95/15790. This TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag—ITO electrode layer for electron-injection. A device was disclosed in which the ITO side of the Mg—Ag—ITO electrode layer was used as a hole-injecting contact for a second, different color-emitting OLED stacked on top of the TOLED. Each layer in the stacked OLED (SOLED) was independently addressable and emitted its own characteristic color. This colored emission could be transmitted through the adjacently stacked transparent, independently addressable, organic layer, the transparent contacts and the glass substrate, thus allowing the device to emit any color that could be produced by varying the relative output of the red and blue color-emitting layers.

The PCT/US95/15790 application disclosed an integrated SOLED for which both intensity and color could be independently varied and controlled with external power supplies in a color tunable display device. The PCT/US95/15790 application, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Such devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers separating the anode and cathode of the device. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. Recombination of this short-lived state may be visualized as an electron dropping from its conduction potential to a valence band, with relaxation occurring, under certain conditions, preferentially via a photoemissive mechanism. Under this view of the mechanism of operation of typical thin-layer organic devices, the electroluminescent layer comprises a luminescence zone receiving mobile charge carriers (electrons and holes) from each electrode.

The materials that function as the electron transporting layer of the OLED are frequently the same materials that are incorporated into the OLED to produce the electroluminescent emission. Such devices are referred to as having a single heterostructure. Alternatively, the electroluminescent material may be present in a separate emissive layer between the hole transporting layer and the electron transporting layer in what is referred to as a double heterostructure.

A well documented cause of OLED failure is thermally induced deformation of the organic layers (e.g. melting, glass formation, etc.). This failure mode can be seen in the studies that have been carried out with hole transporting materials, K. Naito and A. Miura, J. Phys. Chem. (1993), 97, 6240–6248; S. Tokito, H. Tanaka, A. Okada and Y. Taga. Appl. Phys. Lett. (1996), 69, (7), 878–880; Y. Shirota, T Kobata and N. Noma, Chem. Lett. (1989), 1145–1148; T. Noda, I. Imae, N. Noma and Y. Shirota, Adv. Mater. (1997), 9, No. 3; E. Han, L. Do, M. Fujihira, H. Inada and Y. Shirota, J. Appl. Phys. (1996), 80, (6) 3297–701; T. Noda, H. Ogawa, N. Noma and Y. Shirota, Appl. Phys. Lett. (1997), 70, (6), 699–701; S. Van Slyke, C. Chen and C. Tang, Appl. Phys. Lett. (1996), 69, 15, 2160–2162; and U.S. Pat. No. 5,061,569. The most common hole transporter used in the HTL of OLEDs is a biphenyl bridged diamine, N,N'-diphenyl-N,N'-bis(3-methylphenyl)-1,1-biphenyl-4,4'-diamine (TPD) having the chemical structure:

TPD

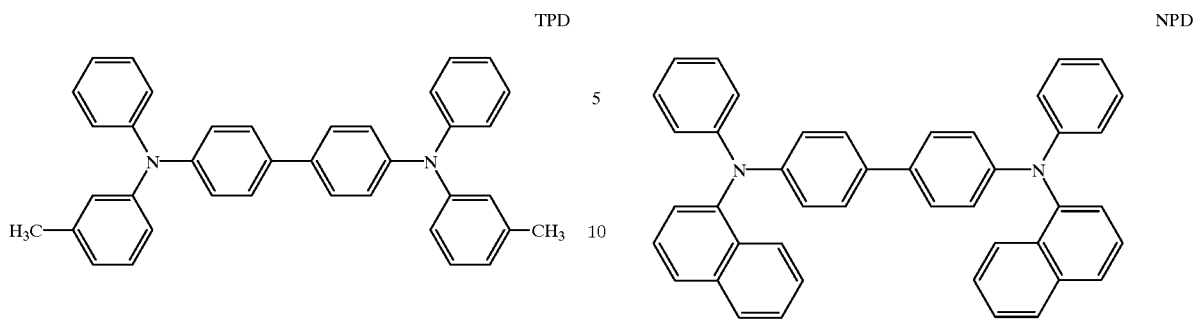

NPD

This material has a melting point of 167° C. and a glass transition temperature of 65° C. If a device prepared with TPD is heated above 65° C., catastrophic irreversible failure results. In order to increase the glass transition temperature of the HTL, several groups have explored different modifications to the basic structure of TPD, Naito et al.; Tokito et al.; Shirota et al.; Noda et al. (Adv. Mater.); Han et al.; Noda et al.(Appl. Phys. Lett.); Van Slyke et al.; and U.S. Pat. No. 5,061,569. While these studies have led to materials with $T_g$ values as high as 150° C., they have not led to an understanding of why certain structural modifications increase $T_g$, while other modifications may not affect $T_g$ at all or may even lower $T_g$. Still other modifications may produce a material not having a glass transition temperature at all or a material not having the combination of properties that is suitable for use in an HTL. For example, replacing the amine groups of TPD with carbazole groups to produce 4,4'-di(N-carbazolo)diphenyl (CBP), having the chemical structure:

CBP

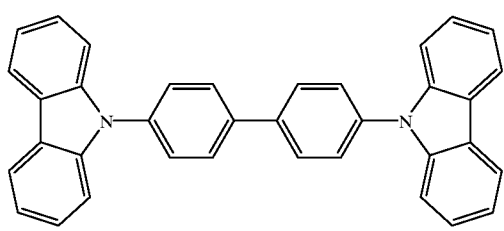

increases the melting point to 285° C. However, the material shows no glass transition. Materials that are present as a glass are desirable for use in the HTL of an OLED, rather than as a crystalline or polycrystalline material, since glasses are capable of providing higher transparency as well as producing superior overall charge carrier characteristics as compared with the polycrystalline materials that are typically produced when thin films of the crystalline form of the materials are prepared.

U.S. Pat. No. 5,061,569 discloses hole transporting materials comprised of at least two tertiary amine moieties and further including an aromatic moiety containing at least two fused aromatic rings attached to the tertiary amine nitrogen atoms. Out of the large number of compounds encompassed by the broadly disclosed class of compounds recited, U.S. Pat. No. 5,061,569 fails to disclose how to select those compounds which have a high glass transition temperature. For example, the naphthyl derivatives do make stable glasses, however, the α-form (containing the 1-substituted naphthyl group), a compound (NPD) having the chemical structure:

was reported to have a $T_g$ (105° C.) which is substantially higher than TPD, while the β-form (containing the 2-substituted naphthyl group), a compound (referred to herein as the β-derivative of NPD) having the structure:

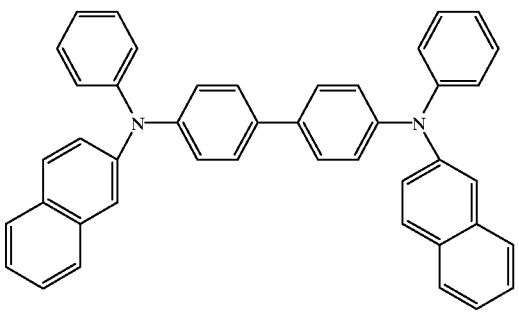

has been generally understood to have a $T_g$ which is substantially lower than α-derivative. Apparently because of this purportedly low and anomalous difference between $T_g$ of the α- β-derivatives, there are no known reports of using the β-derivative as the hole transporting material of an OLED.

It would be desirable if OLED's could be fabricated from glassy charge carrier materials having improved temperature stability, while still providing luminescent characteristics comparable to prior art compounds. In addition, it would be useful to have a method for selecting and preparing such glassy charge carrier materials having improved temperature stability, as characterized, in particular, by glassy charge carrier materials having a high glass transition temperature.

ADVANTAGES AND SUMMARY OF THE INVENTION

The present invention is directed to charge carrier layers comprised of conductive organic materials having improved temperature stability while still being able to provide the high luminescent output desired for OLED's.

In particular, the present invention is directed toward OLEDs comprised of an organic charge carrier layer formed from a charge carrier material that is capable of forming a stable glass due to the presence of a compound having an asymmetric molecular structure in the charge carrier material.

A representative embodiment of the present invention is directed to hole transporting layers comprised of thermally stable asymmetric derivatives of aromatic diamines.

In particular, the present invention is directed to an organic light emitting device comprising a heterostructure for producing electoluminescence wherein the heterostructure is comprised of a charge carrier layer having a glass structure, the charge carrier layer being comprised of a compound having an asymmetric molecular structure, the asymmetric molecular structure being a core atom or core chemical group bonded to at least two charge carrying substituents with at least one of the charge carrying substituents being different from the other charge carrying substituent or substituents.

Further objectives and advantages of the present invention will be apparent to those skilled in the art from the detailed description of the disclosed invention.

DETAILED DESCRIPTION OF THE PREFERRED EMBODIMENTS

Figure 1A:
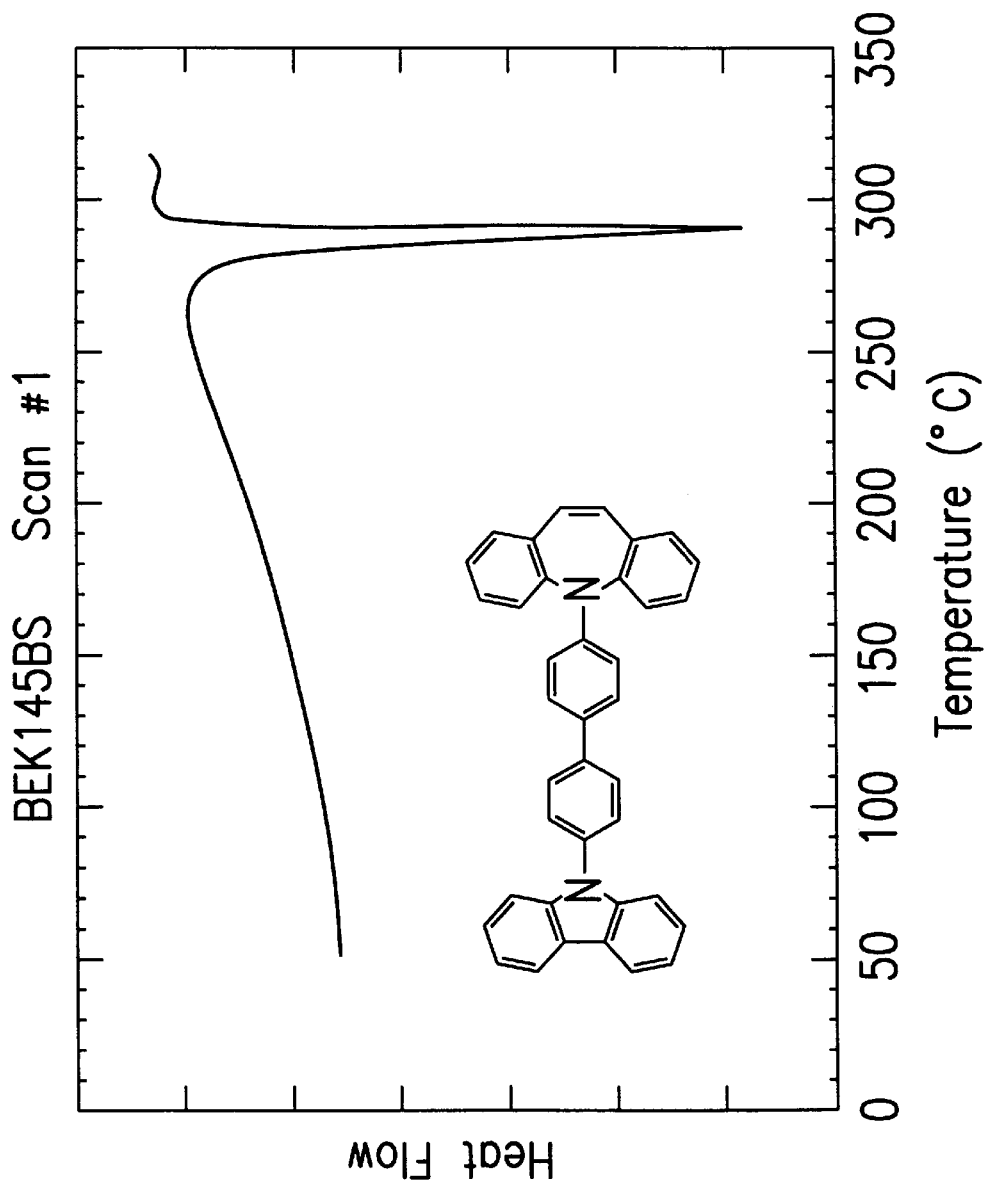
FIGS. 1(a)–1(d) show a sequence of four Differential Scanning Calorimetry (DSC) scans of compound XII. (a) The first DSC scan shows a melt at 290° C. (b) The second DSC scan shows a $T_g$ of 125° C., after which there is a crystallization at approximately 175° C. The scan was stopped at 230° C., before the melt at 290° C. (c) The third DSC scan shows only the melt of the crystalline form at 290° C. (d) The fourth DSC scan again shows the $T_g$ at 125° C., along with the crystallization and melt as before.
Figure 1B:
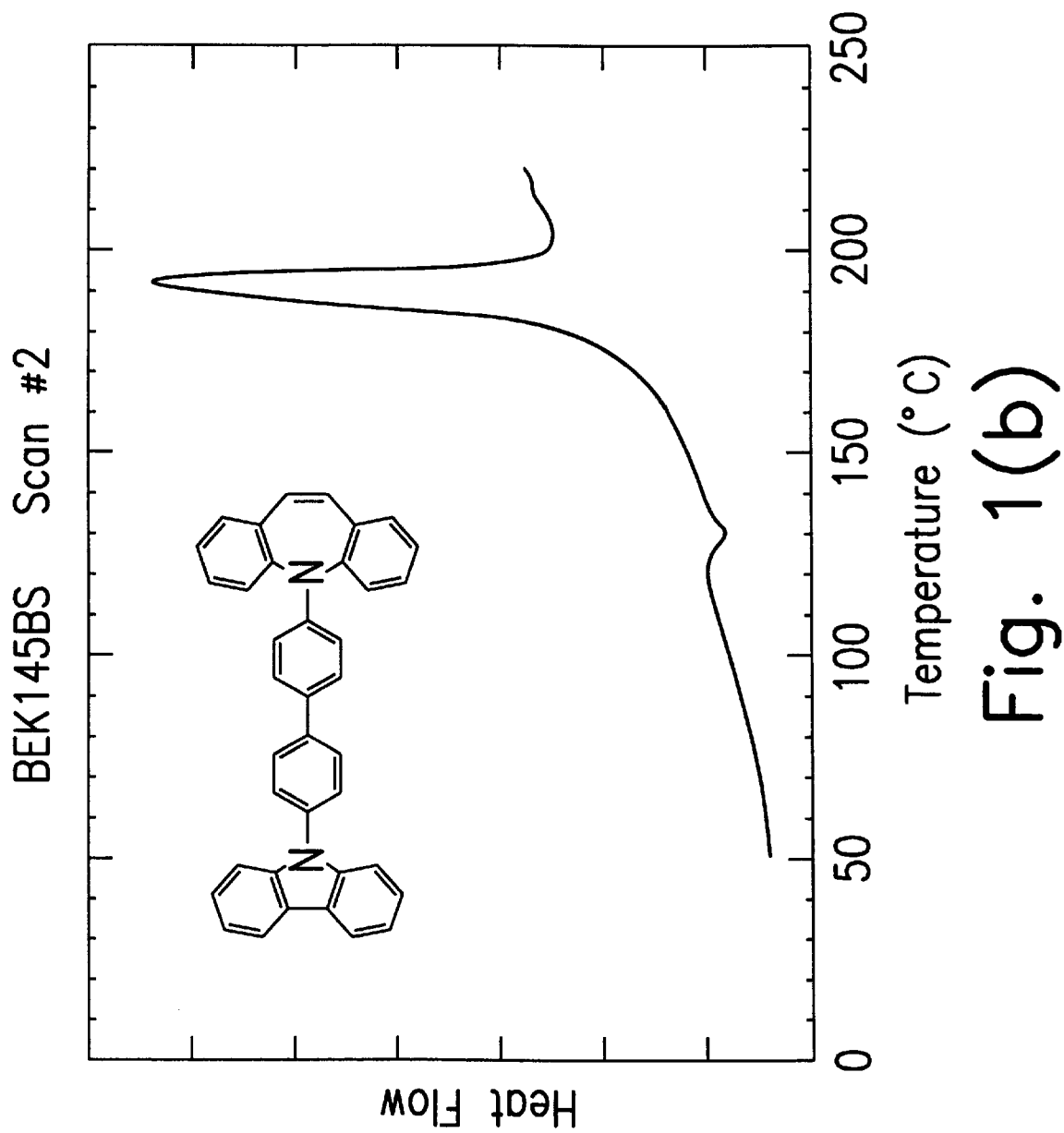
Figure 1C:
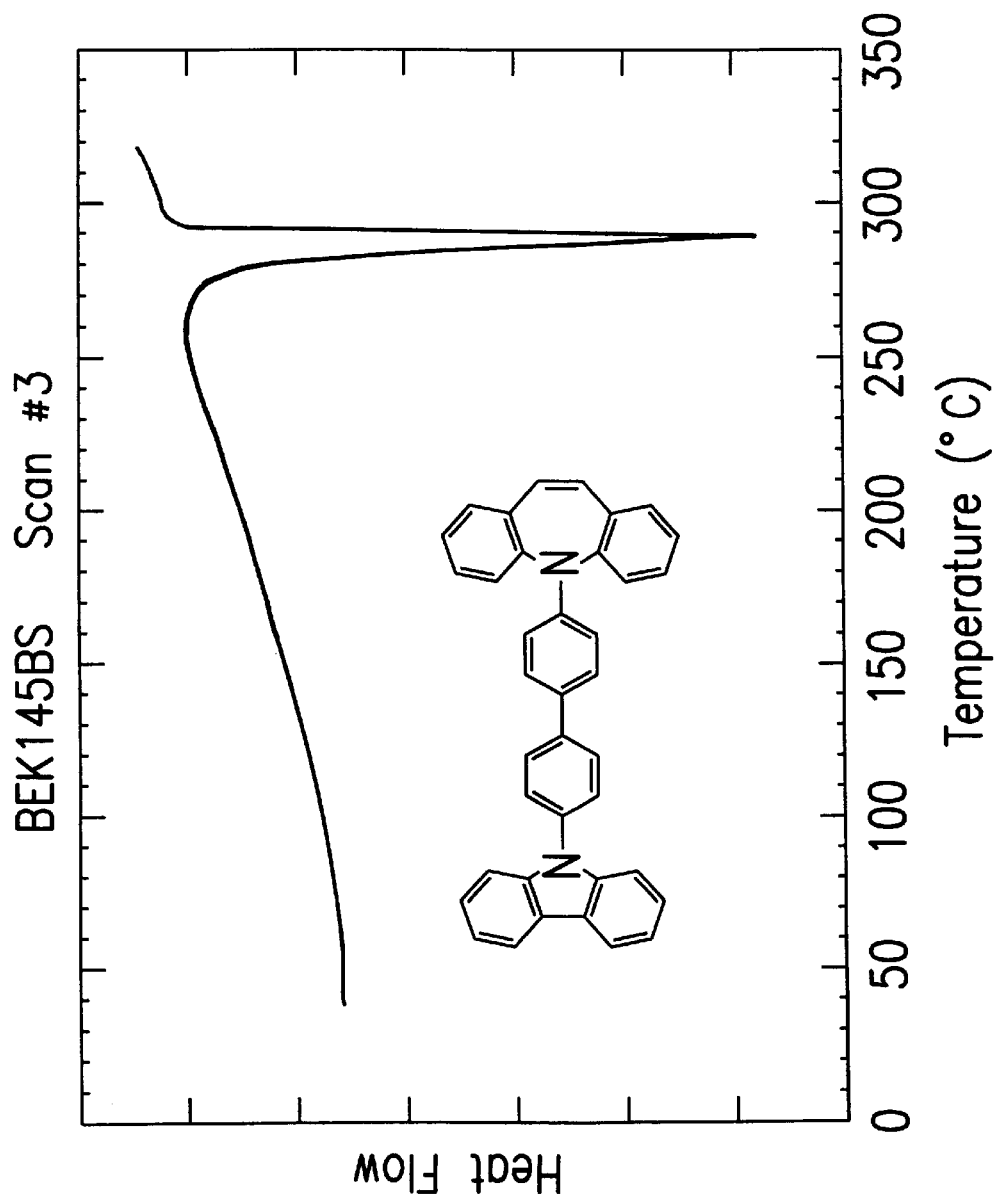
Figure 1D:
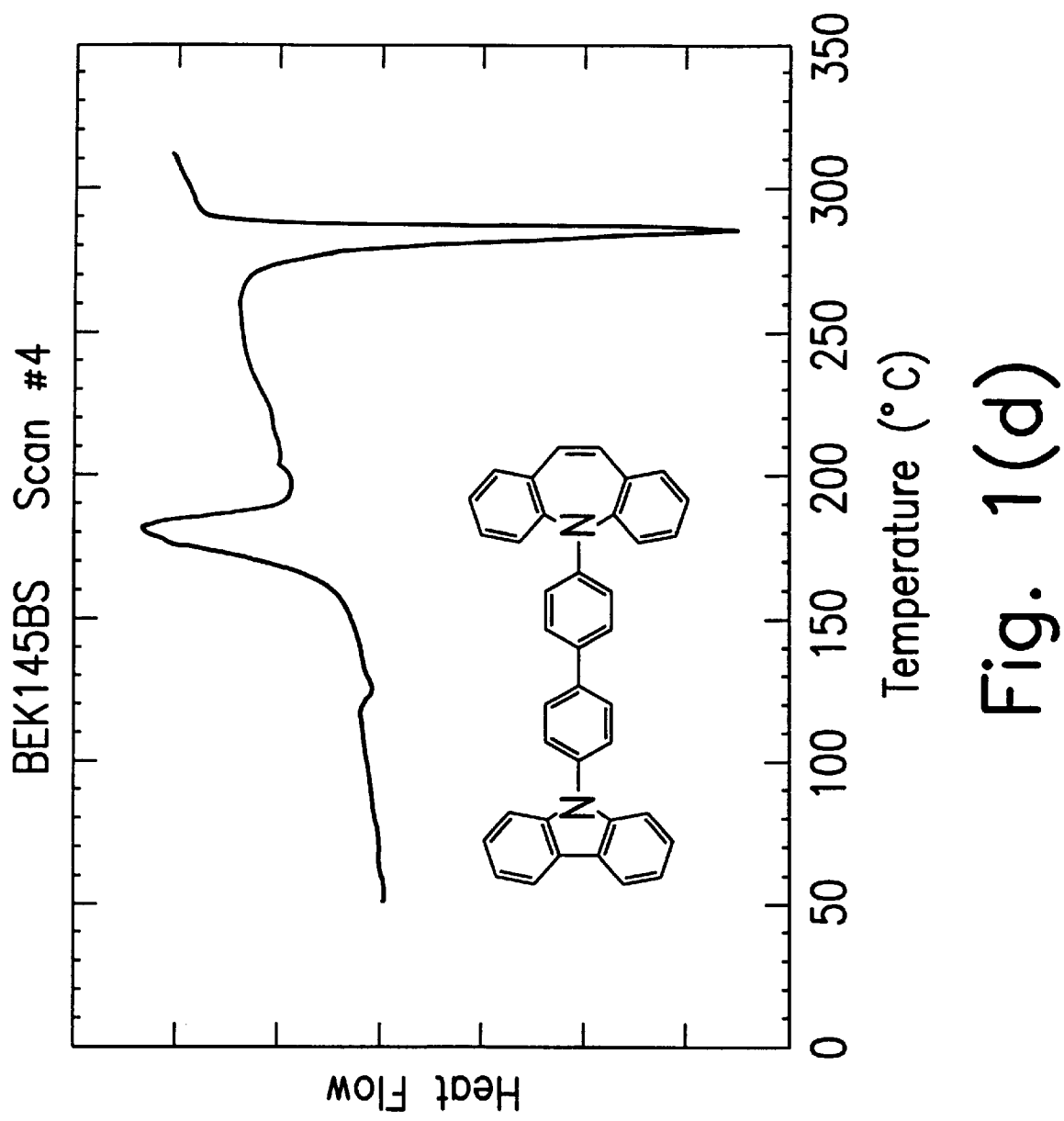

The present invention will now be described in detail for specific preferred embodiments of the invention, it being understood that these embodiments are intended only as illustrative examples and the invention is not to be limited thereto.

The present invention is directed toward OLEDs comprised of an organic charge carrier layer formed from a charge carrier material that is capable of forming a stable glass due to the presence of a compound having an asymmetric molecular structure in the charge carrier material. As used herein, the term "charge carrier layer" may refer to the hole transporting layer, the electron transporting layer or the separate emissive layer of an OLED having a double heterostructure. Such glass-forming charge carrier materials include those for which the charge carrier material is itself a compound having an asymmetric molecular structure as well as those for which the charge carrier material is doped with the compound having the asymmetric molecular structure. In each case, the reduced degree of symmetry makes it more difficult for the molecules to pack themselves into a regular lattice, as compared to charge carrier materials comprised only of totally symmetric molecules. The reduced symmetry results, thus, in a reduced crystallization rate which makes it possible to prepare the charge carrier material as a stable glass. The glass may be prepared by heating the material above its melting point and then cooling it at a sufficiently rapid rate such that crystallization does not occur. In fact, some of the charge carrier materials disclosed herein do not crystallize at all.

While not intending to be limited by any particular theory or mechanism for explaining exactly how or why such charge carrier materials form stable glasses, the present invention is, thus, directed toward designing and synthesizing charge carrier materials comprised of compounds having an asymmetric molecular structure, which inhibits or prevents crystallization of the charge carrier material, such that the charge carrier material can be prepared as a stable glass. Such compounds may be tailored to function as the charge carrier material itself or as a dopant for hindering crystallization in other charge carrier materials. The present invention is further directed to OLEDs containing layers comprised of such glassy charge carrier materials.

The present invention is, in particular, directed to OLEDs containing hole transporting layers comprised of compounds having an asymmetric molecular structure in which hole transporting substituents are asymmetrically located around a core atom or core chemical group. The core chemical group is typically comprised of a phenylene group which is substituted with at least two hole transporting amine groups, wherein at least one of the amine groups is different from at least one other amine group. For example, as a representative embodiment of the present invention, the compound having the asymmetric compound molecular structure may have a single phenylene core, as shown by formula I:

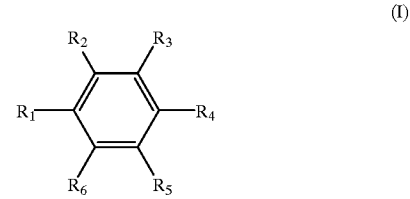

(I)

wherein $R_1$, $R_2$, $R_3$, $R_4$, $R_5$ and $R_6$ are, independently of one another, hole transporting amine groups, or hydrogen, with the proviso that at least two amine groups are present and at least one amine group is different from at least one other amine group. For example, $R_1$ and $R_4$ are hole transporting amine groups wherein $R_1$ is different from $R_4$, and $R_2$, $R_3$, $R_5$ and $R_6$ are each hydrogen.

As another representative embodiment of the present invention, the compound having the asymmetric molecular structure may have a biphenylene core, as represented by formula II:

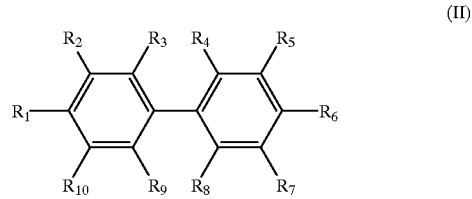

(II)

wherein $R_1$, $R_2$, $R_3$, $R_4$, $R_5$, $R_6$, $R_7$, $R_8$, $R_9$ and $R_{10}$ are, independently of one another, hole transporting amine groups, or hydrogen, with the proviso that at least two amine groups are present and at least one amine group is different from at least one other amine group. For example, $R_1$ and $R_6$ are hole transporting amine groups wherein $R_1$ is different from $R_6$, and $R_2$, $R_3$, $R_4$, $R_5$, $R_7$, $R_8$, $R_9$ and $R_{10}$ are each hydrogen.

The term "hole transporting amine group," as used herein, refers to an amine group which, when present as a substituent in a material contained in a layer of an OLED, causes the material to provide electrical conduction through the layer, when a voltage is applied, preferentially by conduction of holes, as distinct from electron transporting materials that provide electrical conduction preferentially by the conduction of electrons. Such hole transporting amine groups are typically comprised of nitrogen atoms that are directly bonded to two phenyl groups (in addition to the phenyl group of the phenylene core), wherein the two phenyl groups may be joined so as to form a heterocyclic ring including the nitrogen, for example, a carbazole group, or the two phenyl groups may be unattached to each other. Each phenyl group may itself be fused with still another phenyl group, being bonded to the nitrogen atom, for example, either as a 1-naphthyl group or as a 2-naphthyl group. In particular, the hole transporting amine groups may be selected from the group consisting of:

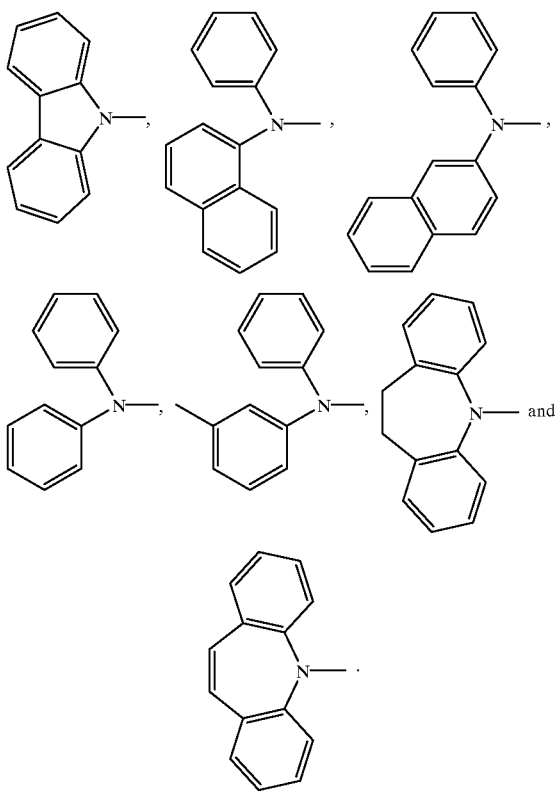

As a representative embodiment of the present invention in which the core atom is a nitrogen atom, the compound may have an asymmetric molecular structure as given by formula III:

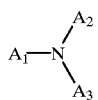

(III)

wherein $A_1$, $A_2$ and $A_3$ are each comprised of amino-substituted phenyl groups, which produce a hole transporting aryl amine functionality, with the proviso that $A_1$ is different from $A_2$ and $A_3$. The phenyl groups of $A_2$ and $A_3$ may be joined so as to form a heterocyclic ring including the nitrogen, e.g., so as to constitute a carbazole group, or the phenyl groups of $A_2$ and $A_3$ may be unattached to each other. Each phenyl group may itself be fused with still another phenyl group and bonded to the nitrogen atom either, for example, as a 1-naphthyl group or as a 2-naphthyl group.

As representative examples of electron transporting compounds, the R- or A-groups of the compounds of formulas I, II or III may be charge carrier groups which, when present as a substituent in a material contained in a layer of an OLED, causes the material to provide electrical conduction through the layer, when a voltage is applied, preferentially by conduction of electrons, for example, an oxadiazole, a triazole, a thiophene or oligothiophene group.

The present invention is, thus, directed to a glass for use in one or more of the charge carrier layers of an OLED, wherein the glass is comprised of a compound having an asymmetric molecular structure, the asymmetric molecules structure being comprised of a core atom or core chemical group that is bonded to at least two charge carrying substituents with at least one of the charge carrying substituents being different from the other substituent or, whenever there is more than one other charge carrying substituent, different from the other substituents. The compound having the asymmetric molecular structure may be the predominant component of the charge carrier layer or the asymmetric compound may be used as a dopant in the charge carrier layer.

While the present invention may typically be directed to compounds in which all the charge carrying substituents either have a hole transporting functionality or all substituents have an electron transporting functionality, glasses containing hybrid compounds comprised of both types of charge carrying substituents also fall fully within the scope and spirit of the present invention, provided that such hybrid compounds do not have dipole moments which significantly inhibit carrier conduction by hindering charge carrier mobility. The present invention is, thus, further directed toward OLED layers comprised of such hybrid compounds. For example, the separate emissive layer of a double heterostructure may be comprised of such a hybrid compound.

As an example of a process related to the present invention, it was discovered that in the initial attempts to fabricate OLEDs using CBP as the hole transporting material, glassy thin films could be grown having promising properties as a hole transporting material in OLEDs based on $Alq_3$ as the electron transporting material. However, when the synthesis of the CBP was scaled up using purified CBP material, the purified material crystallized immediately upon deposition as a thin film and the glassy state of the CBP material could no longer be produced. It was discovered that the initial experiments had been carried out with CBP containing a 2–5% carbazole impurity which prevented crystallization. The carbazole impurity apparently hindered crystallization to a degree sufficient to prevent crystallization of the impure CBP material.

Representative embodiments of the present invention are illustrated by the compounds of formula I and XII, which are listed in Tables 1 and 2, respectively. The thermal properties are shown for each material listed in these tables, wherein "$T_g$=NA (not applicable)" refers to the fact that a crystalline material could not be formed.

Of particular note with respect to the $T_g$ values, the α-β-derivatives of NPD, shown as the symmetric compounds S IX and S X in Table 2, respectively, were measured to have substantially the same $T_g$ values. These results show that, contrary to what has been generally understood to be the case, the β-derivative of NPD may also be useful as the hole transporting material of an OLED. The present invention is, thus, further directed to an OLED comprised of a hole transporting layer comprised of the β-derivative of NPD.

TABLE 1
Compounds having the single phenylene core of formula I.
| $R_1 =$ | \multicolumn{4}{c}{$R_4 =$} |
|---|---|---|---|---|
| | 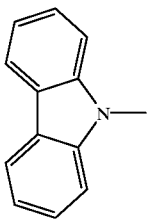 | 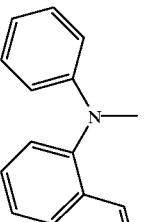 | 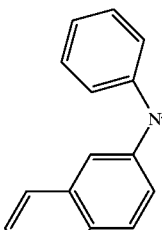 | 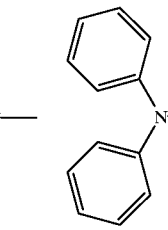 |
| 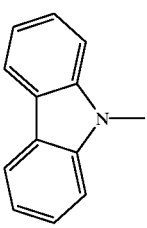 | Mp = 310° C.<br>Tg = NA<br>S I | Mp = 215° C.<br>Tg = 88° C.<br>I | Mp = 212° C.<br>Tg = 83° C.<br>II | Mp = 158° C.<br>Tg = 61°<br>III |
| 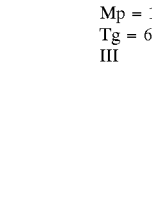 | | Mp = 185° C.<br>Tg = 70° C.<br>S II | | |
| 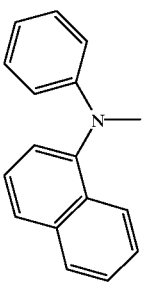 | | | Mp = 184° C.<br>Tg = 70° C.<br>S III | |
| 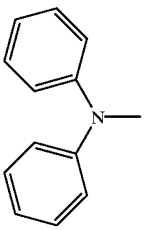 | | | | |

TABLE 1-continued
Compounds having the single phenylene core of formula I.
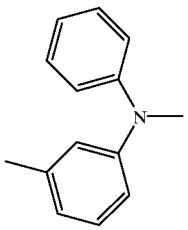
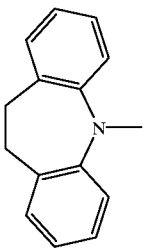
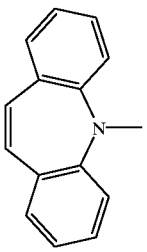
| $R_1 =$ | $R_4 =$ | | |
|---|---|---|---|
| 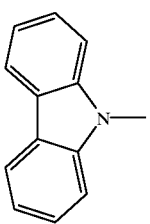 | 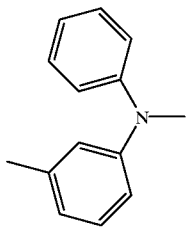<br>Mp = 139° C.<br>Tg = 54° C.<br>IV | 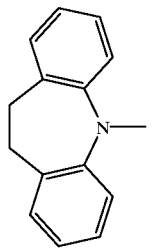<br>Mp = 233° C.<br>Tg = 91° C.<br>V | 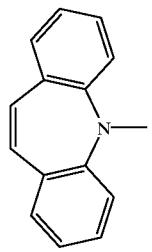<br>Mp = 259° C.<br>Tg = 103° C.<br>VI |

TABLE 1-continued
Compounds having the single phenylene core of formula I.
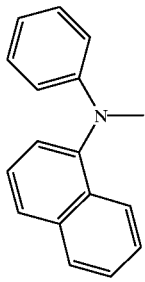
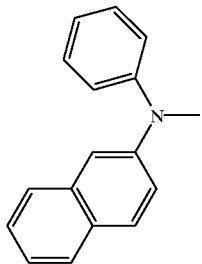
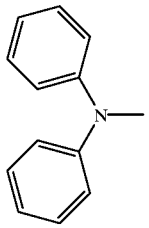
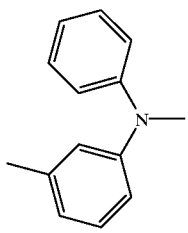
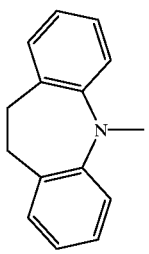

TABLE 1-continued
Compounds having the single phenylene core of formula I.
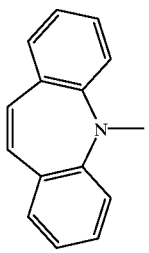
TABLE 2
Compounds having the biphenylene core of formula II
| | $R_6 =$ | | | |
|---|---|---|---|---|
| $R_1 =$ | 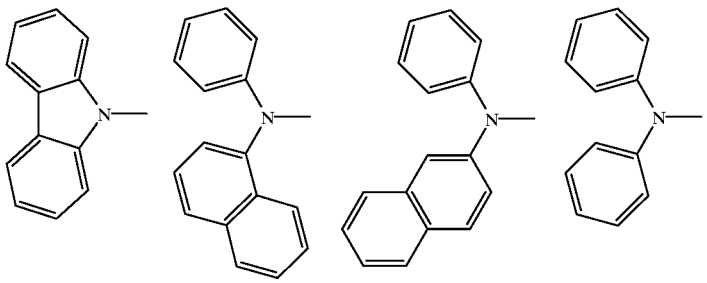 | | | |
| 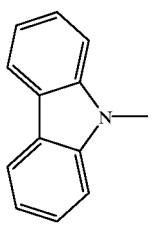 | Mp = 290° C.<br>Tg = NA<br>S VIII | Mp = 253° C.<br>Tg = 109° C.<br>VII | Mp = 249° C.<br>Tg = 107° C.<br>VIII | Mp = 217° C.<br>Tg = 91°<br>IX |
| 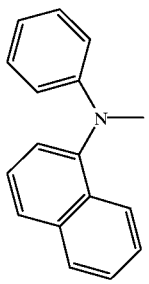 | | Mp = 265° C.<br>Tg = 100° C.<br>S IX | | |
| 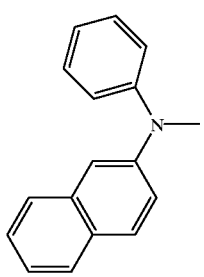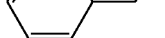 | | | Mp = 266° C.<br>Tg = 101° C.<br>S X | |

TABLE 2-continued
Compounds having the biphenylene core of formula II
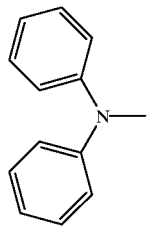
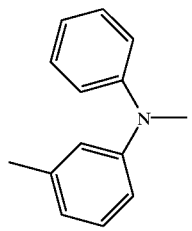
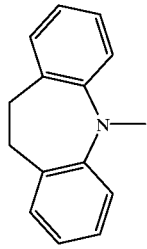
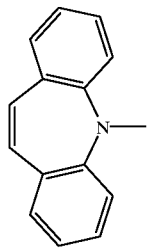
| $R_1 =$ | $R_6 =$ | | |
|---|---|---|---|
| | 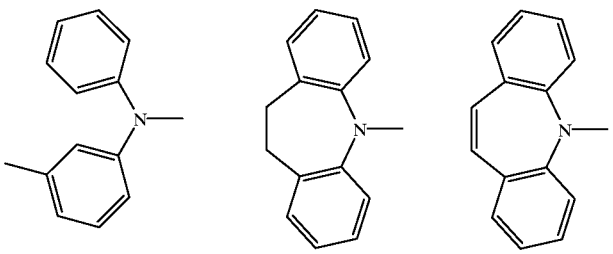 | | |
| 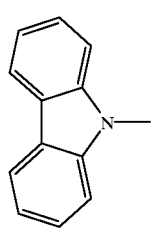 | Mp = 198° C.<br>Tg = 85° C.<br>X | Mp = 273° C.<br>Tg = 117° C.<br>XI | Mp = 291° C.<br>Tg = 125° C.<br>XII |

TABLE 2-continued
Compounds having the biphenylene core of formula II
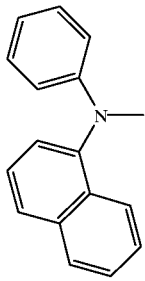
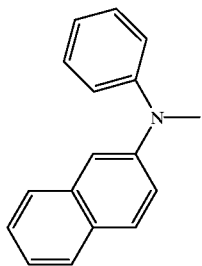
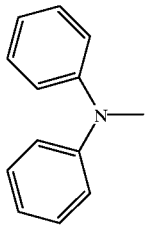
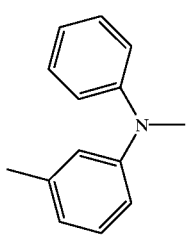
Mp = 175° C.
Tg = 60° C.
S XII
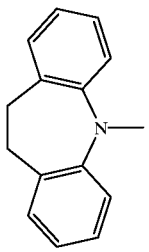

TABLE 2-continued

Compounds having the biphenylene core of formula II

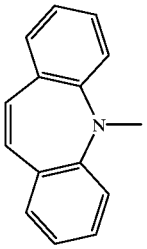

Figure 2A:
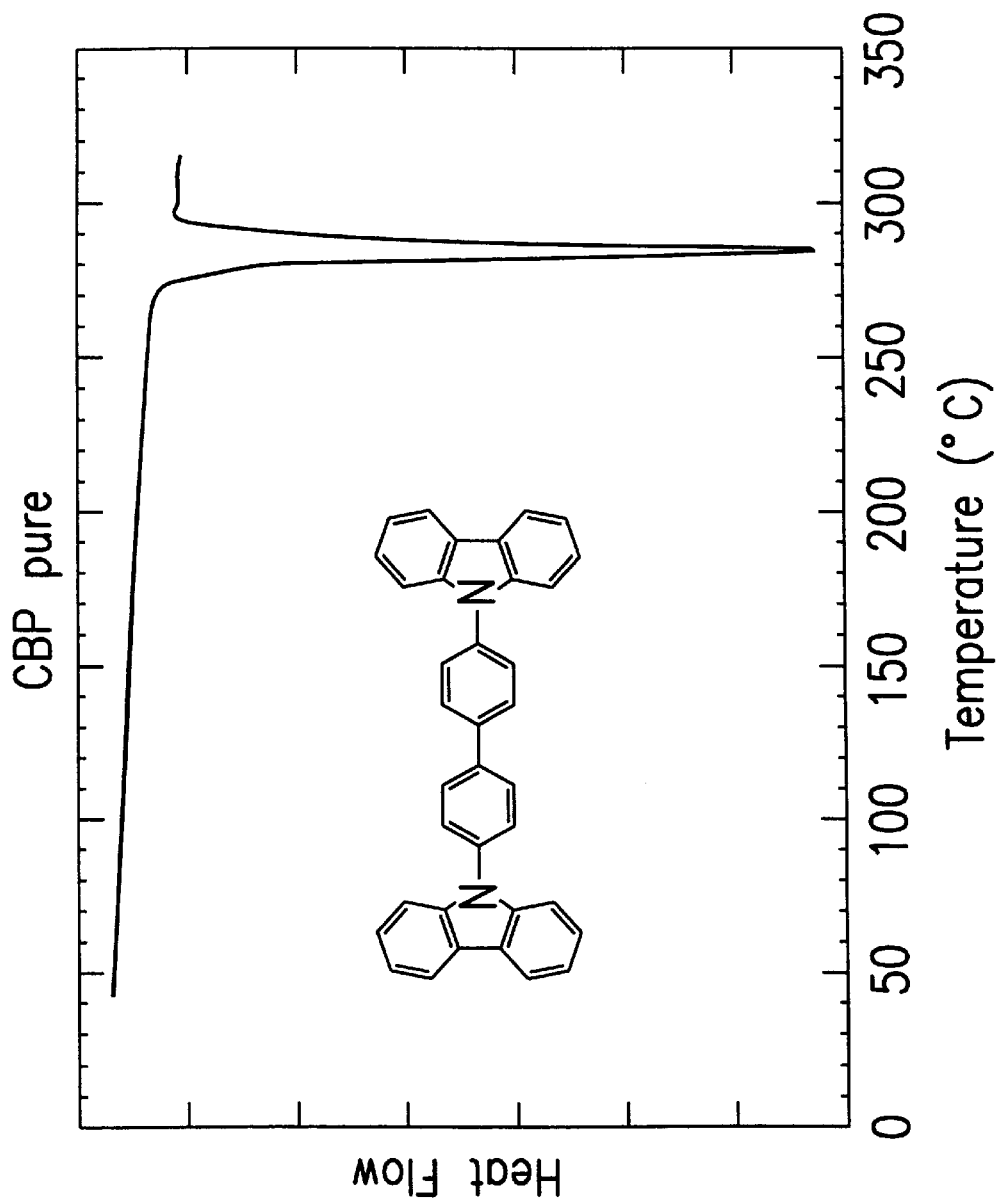
FIGS. 2(a)–2(c) show DSC scans of pure CBP and of a mixture of CBP and 10% compound I. (a) The DSC scan shows a transition temperature that is due to pure CBP. (b) The first DSC scan of the mixture shows the lower melt transition that is due to compound I, and the second transition that is due to CBP. (c) The second DSC scan of the same mixture gives a glass transition at 107° C., after which there is a crystallization at approximately 145° C., along with a melt of CBP at 280° C. The asymmetric compound I stays a glass and does not crystallize, as shown from the absence of the melt corresponding to it in the first scan of the mixture, as shown in FIG. 2(b).
Figure 2B:
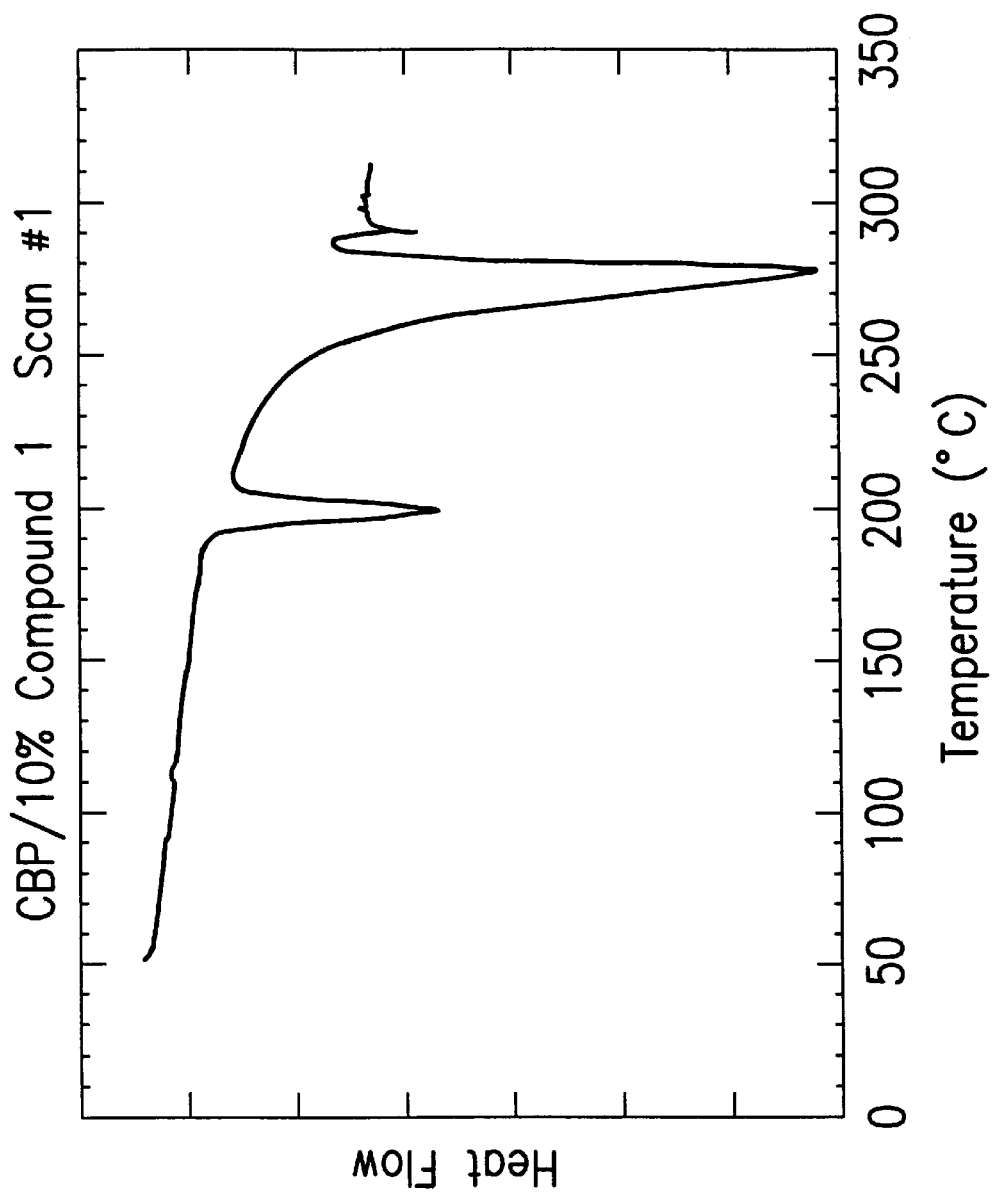
Figure 2C:
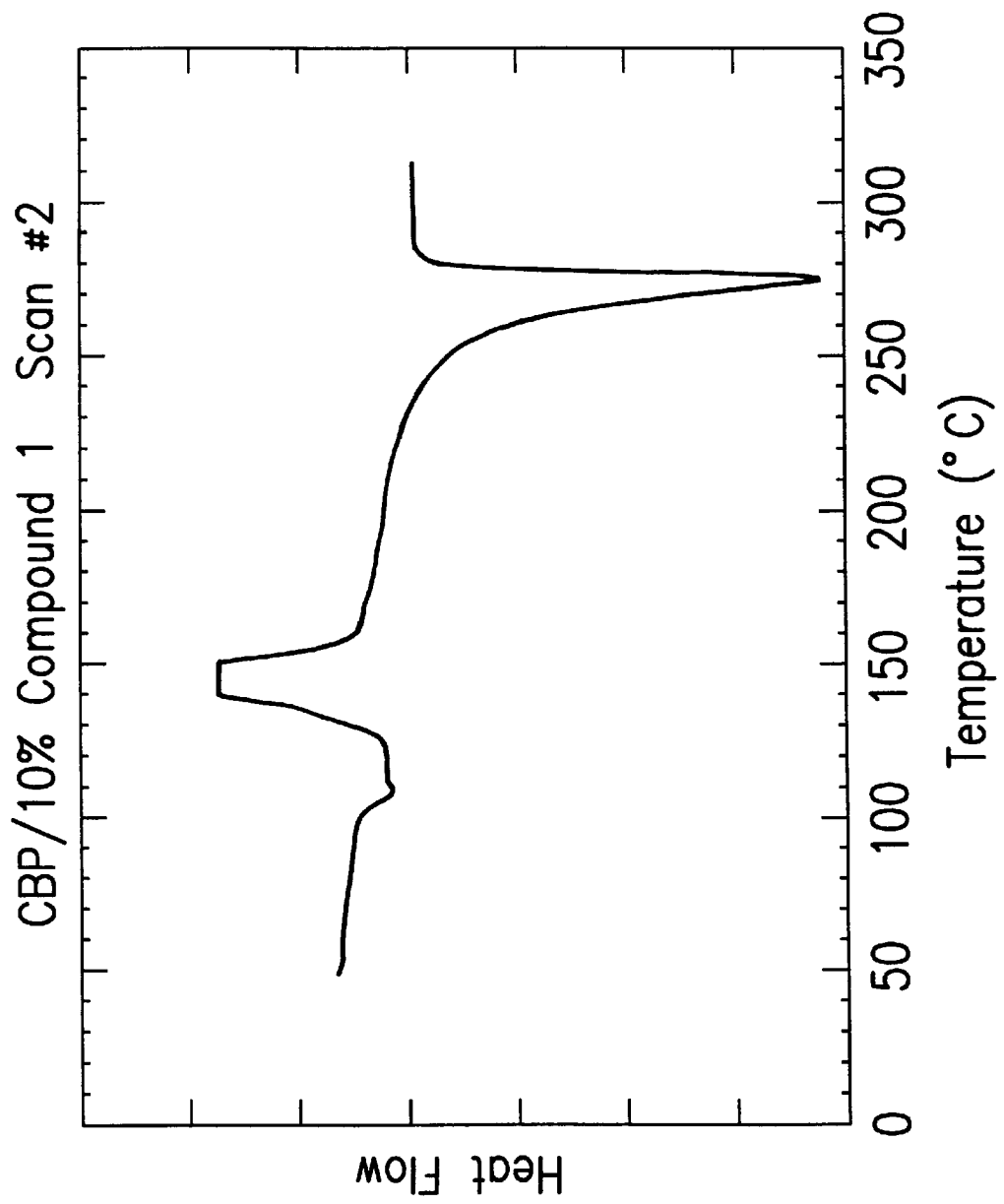

The compounds shown in Tables 1 and 2 have $T_g$ values ranging from 54 to 125° C. Some of these materials have high $T_g$ values (e.g. compounds XI and XII), and may be useful as HTL materials by themselves. The thermal behavior for these asymmetric materials are all very similar, as illustrated in FIG. 2 for the sequence of DSC scans that were run for compound XII. On the first heating cycle, after removing the sample from the sublimation tube in which it was prepared, only a melting transition is observed at 291° C. The sample is then cooled to room temperature and heated again. On the second heating cycle a $T_g$ is observed at 125° C. followed by a crystallization transition at 180° C. and a melt transition at the same temperature as before. If the sample is heated through the $T_g$, but not the recrystallization transition the cycle can be repeated several times. If, however, the sample is heated through the recrystallization transition and then cooled, a $T_g$ is not observed on subsequent reheating.

The explanation for this sequence of observations for each scan is that the sample is initially in a crystalline form on removing it from the sublimation tube. This would typically be expected since the rate of cooling in the sublimation is very slow. On heating the sample through the melt and then cooling rapidly to room temperature, a glass is formed. If this glass is heated through the crystallization transition, the sample converts from a glass to a crystal. If the sample is not heated through the recrystallization transition, the sample remains a glass. Similar behavior is observed for all of the asymmetric materials but, of course, with transitions at different temperatures.

In order to examine how these asymmetric materials perform as crystallization inhibitors a range of different compositions of an asymmetric HTL and CBP were examined. In these experiments, the asymmetric HTL and CBP were mixed and ground together with a mortar and pestle to form a relatively homogeneous sample. When this mixture was heated in the DSC, two melt transitions were observed, one of the asymmetric material and one for CBP. FIG. 2 shows the DSC scans for a mixture of compound I and CBP (10% compound I by weight). The sample in the DSC pan at this point was a solution of compound I in CBP. The sample was cooled from the melt and, on reheating, a $T_g$ of 107° C. and a recrystallization transition at 145° C. was observed. A melt was then observed at 285° C. As representative embodiments of the remaining asymmetric compounds, the thermal behavior for compounds I, IV, VI and VII all produced substantially the same thermal behavior, with substantially the same $T_g$ and recrystallization temperatures as observed for the mixtures shown in FIG. 2. Mixtures were also examined with different ratios of the asymmetric HTL to CBP. Substantially the same thermal behavior was seen for these mixtures as was seen for the 10% mixture, i.e. a $T_g$ of 110–115° C. and recrystallization and melt transitions.

OLEDs could be made from one of these mixtures by two different methods. In one case the materials could be deposited simultaneously from two sources, and in the other case a mixture could be prepared by evaporating a stable ratio or by spin coating a mixed solution.

The OLEDs of the present invention are comprised of a heterostructure for producing electroluminescense which may be fabricated as a single heterostructure or as a double heterostructure. The materials, methods and apparatus for preparing the organic thin films of a single or double heterostructure are disclosed, for example, in U.S. Pat. No. 5,554,220, which is incorporated herein in its entirety by reference. In particular, the present invention is directed toward OLEDs which include a heterostructure for producing electroluminescense wherein the heterostructure includes at least one glassy charge carrier layer comprised of a compound having an asymmetric molecular structure.

As used herein, the term "heterostructure for producing electroluminescense" refers to a heterostructure that includes, for a single heterostructure, a substrate, a hole injecting anode layer in contact with the substrate, a hole transporting layer in contact with the anode layer, an electron transporting layer in contact with the hole transporting layer, and an electrode injecting cathode layer in contact with the hole electron transporting layer. If the cathode layer is a metal cathode layer of Mg:Ag, then a metal protective layer, for example, made of a layer of Ag for protecting the Mg:Ag cathode layer from atmospheric oxidation, may also be present. If a double heterostructure is used to produce electroluminescense, a separate emissive layer is included between the hole transporting layer and the electron transporting layer.

Whenever the OLED is comprised of a double heterostructure having an additional layer of emissive material between the hole transporting and electron transporting layers, this additional layer is referred to as a "separate emissive layer" so as to distinguish it from the electron transporting layer of a single heterostructure that functions both as the electron transporting layer as well as the emissive layer that produces the electroluminescense. The term "emissive layer" as used herein, thus, may refer either to the emissive, electron transporting layer of a single heterostructure or the separate emissive layer of a double heterostructure.

Alternatively, the heterostructure for producing electroluminescense may have an inverted (IOLED) structure in which the sequence of layers deposited on the substrate is inverted, that is, an electron injecting cathode layer is in direct contact with the substrate, an electron transporting layer is in contact with the cathode layer, a hole transporting layer is in contact with the electron transporting layer, and a hole injecting anode layer is in contact with the hole transporting layer.

If the heterostructure for producing electroluminescense is included as part of a stacked OLED (SOLED), one or both of the electrodes of an individual heterostructure may be in contact with an electrode of an adjacent heterostructure. Alternatively, dependent on the circuitry used to drive the SOLED, an insulating layer may be provided between adjacent electrodes of two of the OLEDs in the stack.

The single or double heterostructures as referred to herein are intended solely as examples for showing how an OLED embodying the present invention may be fabricated without in any way intending the invention to be limited to the particular materials or sequence for making the layers shown. For example, a single heterostructure typically includes a substrate which may be opaque or transparent, rigid or flexible, and/or plastic, metal or glass; a first electrode, which is typically a high work function, hole-injecting anode layer, for example, an indium tin oxide (ITO) anode layer; a hole transporting layer; an electron transporting layer; and a second electrode layer, for example, a low work function, electron-injecting, metal cathode layer of a magnesium-silver alloy, (Mg:Ag) or of a lithium-aluminum alloy, (Li:Al).

Materials that may be used as the substrate in a representative embodiment of the present invention include, in particular, glass, transparent polymer such as polyester, sapphire or quartz, or substantially any other material that may be used as the substrate of an OLED.

Materials that may be used as the hole-injecting anode layer in a representative embodiment of the present invention include, in particular, ITO, Zn—In—$SnO_2$ or $SbO_2$, or substantially any other material that may be used as the hole-injecting anode layer of an OLED.

In addition to the materials as disclosed herein for use in the hole transporting layer or in the electron transporting layer, other materials that may be used in the hole transporting layer in a representative embodiment of the present invention include, in particular, N,N'-diphenyl-N,N'-bis(3-methylphenyl)1-1'biphenyl-4,4'diamine (TPD), 4,4'-bis[N-(1-naphthyl)-N-phenyl-amino]biphenyl ($\alpha$-NPD) or 4,4'-bis[N-(2-naphthyl)-N-phenyl-amino]biphenyl ($\beta$-NPD). Other materials that may be used as the electron transporting layer include, in particular, tris-(8-hydroxyquinoline)-aluminum ($Alq_3$) and carbazole. Other materials that may be used as the separate emissive layer, if present, include, in particular, dye-doped $Alq_3$, or substantially any other material that may be used as the separate emissive layer of an OLED.

Materials that may be used as the electron-injecting, metal cathode layer in a representative embodiment of the present invention include, in particular, Mg—Ag, Li—Ag or Ca, or substantially any other material that may be used as the cathode layer of an OLED.

The insulating layer, if present, may be comprised of an insulating material such as $SiO_2$, $SiN_x$ or $AlO_2$, or substantially any other material that may be used as the insulating material of an OLED, which may be deposited by a variety of processes such as plasma enhanced chemical vapor deposition (PECVD), electron beam, etc.

The OLEDs of the present invention have the advantage that they can be fabricated entirely from vacuum-deposited molecular organic materials as distinct, for example, from OLEDs in which some of the layers are comprised of polymeric materials, which cannot be readily deposited using vacuum deposition techniques. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as $10\mu$, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 Å (1 Å=$10^{-8}$ cm) to greater than about 4000 Å thick; the hole transporting layer from about 50 Å to greater than about 1000 Å thick; the separate emissive layer of a double heterostructure, if present, from about 50 Å to about 200 Å thick; the electron transporting layer from about 50 Å to about 1000 Å thick; and the metal cathode layer from about 50 Å to greater than about 100 Å thick, or substantially thicker if the cathode layer includes a protective silver layer and is opaque.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED is comprised of a heterostructure which includes at least one glassy charge carrier layer comprised of a compound having an asymmetric molecular structure.

The present invention as disclosed herein may be used in conjunction with co-pending applications: "High Reliability, High Efficiency, Integratable Organic Light Emitting Devices and Methods of Producing Same", Serial No. 08/774,119 (filed Dec. 23, 1996), now U.S. Pat. No. 6,046,543; "Novel Materials for Multicolor Light Emitting Diodes", Ser. No. 08/850,264 (filed May 2, 1997), now U.S. Pat. No. 6,045,930; "Electron Transporting and Light Emitting Layers Based on Organic Free Radicals", Ser. No. 08/774,120 (filed Dec. 23, 1996), now U.S. Pat. No. 5,811,833; "Multicolor Display Devices", Ser. No. 08/772,333 (filed Dec. 23, 1996), now U.S. Pat. No. 6,013,982; "Red-Emitting Organic Light Emitting Devices (OLED's)", Ser. No. 08/774,087 (filed Dec. 23, 1996), now U.S. Pat. No. 6,048,630; "Driving Circuit For Stacked Organic Light Emitting Devices", Ser. No. 08/792,050 (filed Feb. 3, 1997), now U.S. Pat. No. 5,757,139; "High Efficiency Organic Light Emitting Device Structures", Ser. No. 08/772,332 (filed Dec. 23, 1996), now U.S. Pat. No. 5,834,893; "Vacuum Deposited, Non-Polymeric Flexible Organic Light Emitting Devices", Ser. No. 08/789,319 (filed Jan. 23, 1997), now U.S. Pat. No. 5,844,363; "Displays Having Mesa Pixel Configuration", Ser. No. 08/794,595 (filed Feb. 3, 1997), now U.S. Pat. No. 6,091,195; "Stacked Organic Light Emitting Devices", Ser. No. 08/792,046 (filed Feb. 3, 1997), now U.S. Pat. No. 5,917,280; "High Contrast Transparent Organic Light Emitting Device Display", Ser. No. 08/821,380 (filed Mar. 20, 1997), now U.S. Pat. No. 5,986,401; "Organic Light Emitting Devices Containing A Metal Complex of 5-Hydroxy-Quinoxaline as A Host Material", Ser. No. 08/838,099 (filed Apr. 15, 1997), now U.S. Pat. No. 5,861,219; "Light Emitting Devices Having High Brightness", Ser. No. 08/844,353 (filed Apr. 18, 1997), now U.S. Pat. No. 6,125,226; "Organic Semiconductor Laser", Ser. No. 08/859,468 (filed May 19, 1997), now U.S. Pat. No. 6,111,902; "Saturated Full Color Stacked Organic Light Emitting Devices", Ser. No. 08/858,994 (filed on May 20, 1997), now U.S. Pat. No. 5,932,895; "Plasma Treatment of Conductive Layers", PCT/US97/10252, (filed Jun. 12, 1997); "Novel Materials for Multicolor Light Emitting Diodes", Ser. No. 08/814,976, (filed Mar. 11, 1997), abandoned; "Novel Materials for Multicolor Light Emitting Diodes", Ser. No. 08/771,815, (filed Dec. 23, 1996), converted to provisional application Ser. No. 60/072,095, expired; "Patterning of Thin Films for the Fabrication of Organic Multi-color Displays", PCT/US97/10289, (filed Jun. 12, 1997), and "Double Heterostructure Infrared and Vertical Cavity Surface Emitting Organic Lasers", Provisional Ser. No. 60/053,176 (filed Jul. 18, 1997), each co-pending application being incorporated herein by reference in its entirety. The subject invention may also be used in conjunction with the subject matter of each of co-pending U.S. patent application Ser. Nos. 08/354,674, 08/613,207, 08/632,322, now U.S. Pat. Nos. 5,707,745, 5,703,436, 5,757,026 (respectively), and Ser. No. 08/693,359 and provisional patent application Ser. Nos. 60/010,013, expired, 60/024,001, expired, and 60/025,501, expired, each of which is also incorporated herein by reference in its entirety, each co-pending application being incorporated herein by reference in its entirety. The present invention may also be used in conjunction with the subject matter of each of provisional patent application Ser. No. 60/046,061, expired, and the provisional patent application entitled "Double Heterostructure Infrared and Vertical Cavity Surface Emitting Organic Lasers", filed Jul. 18, 1997, Provisional Ser. No. 60/053,176 each of which is also incorporated herein by reference in its entirety.

The materials that may be used as the substrate, the hole-injecting anode layer, the hole transporting layer, the electron transporting layer, the electron-injecting, metal cathode layer, the separate emissive layer if present, or the insulating layer, if present, include the materials as disclosed in these co-pending applications.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

AN EXAMPLE OF THE INVENTION

The following compounds were prepared:
Intermediates
(1) 4-Bromo-N-phenylcarbazole A reaction vessel was charged with 4.37 mmol (4.00 g) $Pd_2dba_3$, (dba=dibenzoylacetone), 6.55 mmol (3.63 g) dppf (dppf=diphenylphosphine ferrocene), and 400 ml dry toluene. Using a magnetic stir bar and hot plate, the mixture was stirred for 15 minutes under argon. Then 436 mmol (48.92 g) sodium t-butoxide was added against counter flow of argon and the reaction was stirred another 30 minutes. Then 291 mmol (48.66 g) carbazole with 873 mmol (205.96 g) 1,4-dibromobenzene were added and the reaction was heated to 100° C. for 16 hours. The reaction progress was followed by TLC until no carbazole could be detected. At end of reaction, the reaction mixture was taken up into water/ether (2:1). The mixture was then washed with water until the organic layer was colorless, then the solution was concentrated. The residue was dissolved in a mixture of toluene/hexane and passed through a short column of silica gel. The solvent was then removed from the column filtrate which yielded the product.

(2) 4-bromo-4'-N-carbazolebiphenyl

Prepared as above using following amounts and using 4,4'-dibromobiphenyl instead of 1,4-dibromobenzene. Reagents and amounts were: 5.98 mmol (1.00 g) carbazole, 17.94 mmol (5.598 g) 4,4'-dibromobiphenyl, 0.0897 mmol (0.082 g) $Pd_2dba_3$, 0.1345 mmol (0.075 g) dppf, 8.97 mmol (1.006 g) sodium t-butoxide and 50 ml toluene as solvent.

Upon completion of the reaction, the reaction mixture was precipitated by addition to 150 ml hexane. This solid was filtered, washed with hexane, and dried. The excess 4,4'-dibromobiphenyl was removed by sublimation at 150° C., leaving the product.

Asymmetric Final Products

Compound I was prepared as above except using the following amounts and using intermediate (1) for the halogenated aryl moiety. Reagents and amounts are, 3.104 mmol (0.681 g) 1-naphthyl-phenyl amine, 3.104 mmol (1.00 g) of intermediate (1), 0.0466 mmol (0.043 g) $Pd_2dba_3$, 0.0698 mmol (0.039 g) dppf, 4.66 mmol (0.522 g) sodium t-butoxide, and 15 ml toulene. Purification of the asymmetric products was as above except that the product itself was sublimed from the filtered solid.

Compound II was prepared as above except using the following amounts and using intermediate (1) for the halogenated aryl moiety. Reagents and amounts are, 3,104 mmol (0.681 g) 2-naphthyl-phenyl amine, 3,104 mmol (1.00 g) of intermediate (1), 0.0466 mmol (0.043 g) $Pd_2dba_3$, 0.0698 mmol (0.039 g) dppf, 4.66 mmol (0.522 g) sodium t-butoxide, and 20 ml tolune. Purified as above.

Compound III was prepared as above except using the following amounts and using intermediate (1) for the halogenated aryl moiety. Reagents and amounts are, 3,104 mmol (0.525 g) diphenyl amine, 3.104 mmol (1.00 g) of intermediate (1), 0.0466 mmol (0.043 g) $Pd_2dba_3$, 0.0698 Mmol (0.039 g) dppf, 4.66 (0.522 g) sodium t-butoxide, and 20 ml toluene. Purified as above.

Compound IV was prepared as above except using the following amounts and using intermediate (1) for the halogenated aryl moiety. Reagents and amounts are, 3,104 mmol (0.509 g) phenyl-o-tolyl amine, mine, 3.104 mmol (1.00 g) of intermediate (1), 0.0466 mmol (0.043 g) $Pd_2dba_3$, 0.0698 mmol (0.039 g) dppf, 4.66 mmol (0.522 g) sodium t-butoxide, and 20 ml toluene. Purified as above.

Compound V was prepared as above except using the following amounts and using intermediate (1) for the halogenated aryl moiety. Reagents and amounts are, 3.104 mmol (0.606 g) iminodibenzyl, 3.104 mmol (1.00 g) of intermediate (1), 0.0466 mmol (0.043 g) $Pd_2dba_3$, 0.0698 mmol (0.039 g) dppf, 4.66 mmol (0.522 g) sodium t-butoxide, and 20 ml toluene. Purified as above.

Compound VI was prepared as above except using the following amounts and using intermediate (1) for the halogenated aryl moiety. Reagents and amounts are, 3.104 mmol (0.600 g) iminostilbene, 3.104 mmol (1.00 g) of intermediate (1), 0.0466 mmol (0.043 g) $Pd_2dba_3$, 0.0698 mmol (0.039 g) dppf, 4.66 mmol (0.522 g) sodium t-butoxide, and 20 ml toluene. Purified as above.

Compound VII was prepared as above except using the following amounts and using intermediate (2) for the halogenated aryl moiety. Reagents and amounts are, 1.26 mmol (0.275 g) 1-naphthyl-phenyl amine, 1.26 mmol (0.500 g) of intermediate (2), 0.0189 mmol (0.017 g) $Pd_2dba_3$, 0.0284 mmol (0.016 g) dppf, 1.89 mmol (0.182 g) sodium t-butoxide, and 15 ml toluene. Purified as above.

Compound VIII was prepared as above except using the following amounts and using intermediate (2) for the halogenated aryl moiety. Reagents and amounts are, 1.26 mmol (0.275 g) 2-naphthyl-phenyl amine, 1.26 mmol (0.500 g) of intermediate (2), 0.0189 mmol (0.017 g) $Pd_2dba_3$, 0.0284 mmol (0.016 g) dppf, 1.89 mmol (0.182 g) sodium t-butoxide, and 15 ml toluene. Purified as above Compound IX was prepared as above except using the following amounts and using intermediate (2) for the halogenated aryl moiety. Reagents and amounts are, 0.992 mmol (0.162 g) diphenyl amine, 0.992 mmol (0.395 g) of intermediate (2), 0.0149 mmol (0.014 g) $Pd_2dba_3$, 0.0223 mmol (0.012 g) dppf, 1.49 mmol (0.143 g) sodium t-butoxide, and 15 ml toluene. Purified as above.

Compound X was prepared as above except using the following amounts and using intermediate (2) for the halogenated aryl moiety. Reagents and amounts are, 1.26 mmol (0.230 g) phenyl-o-tolyl amine, 1.26 mmol (0.500 g) of intermediate (2), 0.0189 mmol (0.017 g) $Pd_2dba_3$, 0.0284 mmol (0.016 g) dppf, 1.89 mmol (0.182 g) sodium t-butoxide, and 15 ml toluene. Purified as above.

Compound XI was prepared as above except using the following amounts and using intermediate (2) for the halogenated aryl moiety. Reagents and amounts are, 0.934 mmol (0.182 g) iminodibenzyl, 0.934 mmol (0.367 g) of intermediate (2), 0.0141 mmol (0.013 g) $Pd_2dba_3$, 0.0234 mmol (0.012 g) dppf, 1.40 mmol (0.135 g) sodium t-butoxide, and 10 ml toluene. Purified as above.

Compound XII was prepared as above except using the following amounts and using intermediate (2) for the halogenated aryl moiety. Reagents and amounts are, 0.928 mmol (0.180 g) iminostilbene, 0.928 mmol (0.370 g) of intermediate (2), 0.0141 mmol (0.013 g) $Pd_2dba_3$, 0.0234 mmol (0.012 g) dppf, 1.39 mmol (0.134 g) sodium t-butoxide, and 10 ml toluene. Purified as above.

Symmetric Final Products

General procedure: Prepared by reacting a secondary aromatic amine (2 equivalents) with 1,4-diiodobenzene (1 equivalent). The above were added to a round bottom flask fitted with a condenser, along with powdered copper (1 equivalent), $K_2CO_3$ (2 equivalents), 18-crown-6 ether (0.15 equivalents), and o-dichlorobenzene. The reaction was heated to 185° C. and then reflexed under argon for 24 hours. The reaction mixture was filtered hot and the filtrate was put under vacuum to remove the solvent. The residue was then passed through a short column of silica gel in toluene. The solvent was then removed from the column filtrate and the solid left behind was sublimed for purification.

Compound S I—Prepared as according to general procedure.

Compound S II—Prepared according to general procedure with the following amounts of reagents. Reagents and amounts are 117.1 mmol (25.670 g) phenyl-1-naphthylamine, 58.6 mmol (19.330 g) diiodobenzene, 144.7 mmol (20.00 g) potassium carbonate, 117.1 mmol (7.44 g) copper powder, 5.82 mmol (1.54 g) 18-crown-6 ether, and 40 ml o-dichlorobenzene. Sublimes at 295° C. under a vacuum of 0.01 Torr.

Compound S III—Prepared according to general procedure. Reagents and amounts are 117.1 mmol (25.670 g) phenyl-2-naphthylamine, 58.6 mmol (19.330 g) diiodobenzene, 144.7 mmol (20.00 g) potassium carbonate, 117.1 mmol (7.44 g) copper powder, 5.82 mmol (1.54 g) 18-crown-6 ether, and 40 ml o-dichlorobenzene. Sublimes at 295° C. under a vacuum of 0.01 Torr.

Compound S VIII—Prepared according to general procedure.

Compound S IX—Prepared according to general procedure with the following amounts of reagents. Reagents and amounts are 174 mmol (38.102 g) phenyl-1-naphthylamine, 62.5 mmol (25.397 g) 4,4'-diiodobiphenyl, 175 mmol (24.268 g) potassium carbonate, 105 mmol (6.706 g) copper powder, 12.9 mmol (3.414 g) 18-crown-6 ether, and 60 ml o-dichlorobenzene. Sublimes at 300° C. under a vacuum of 0.0001 Torr.

Compound S X—Prepared according to general procedure with the following amounts of reagents. Reagents and amounts are 68.4 mmol (15.005 g) phenyl-2-naphthylamine, 34.5 mmol (14.008 g) 4,4'-diiodobiphenyl, 68.5 mmol (9.484 g) potassium carbonate, 45.1 mmol (2.871 g) copper powder, 3.7 mmol (0.984 g) 18-crown-6 ether, and 30 ml o-dichlorobenzene. Sublimes at 300° C. under a vacuum of 0.0001 Torr.

Compound S XII—Prepared as according to general procedure.

Compound S XIII—Prepared according to general procedure with the following amounts of reagents. Reagents and amounts are 51 mmol (10.000 g) iminodibenzyl, 17 mmol (6.94 g) 4,4'-diiodobiphenyl, 68 mmol (9.398 g) potassium carbonate, 34 mmol (2.16 g) copper powder, 2 mmol (0.530 g) 18-crown-6 ether, and 20 ml o-dichlorobenzene. Sublimes at 220° C. under a vacuum of 0.01 Torr.

Procedures for Fabrication of Organic Light-Emitting Devices (OLEDs)

Chemicals

The hole transporting material compound VII was prepared, as described above, by Ullman coupling, and the electron transporting material $Alq_3$ was synthesized according to literature procedure. All materials were sublimed before use.

Procedures

The ITO/Borosilicate substrates (100Ω/square) were cleaned by sonicating with detergent for five minutes followed by rinsing with deionized water. They were then treated twice in boiling 1,1,1-trichloroethane for two minutes. The substrates were then sonicated twice with acetone for two minutes and twice with methanol for two minutes.

The background pressure prior to deposition was $8 \times 10^{-7}$ torr and the pressure during the deposition was around $5 \times 10^{-7}$ to $2 \times 10^{-6}$ torr.

The chemicals were sublimed from resistively heated tantalum boats, and then deposited at a rate from 1 to 3.6 Å/s. The thickness was controlled at 300 Å.

The electron transporting layer ($Alq_3$) was deposited at a rate between 1 to 3.3 Å/s. The total thickness of this layer was controlled at 450 Å.

The substrates were then released to air and masks were put directly on the substrates. The masks are made of stainless steel sheet and contain holes with diameters of 0.25, 0.5, 0.75, and 1.0 mm. The substrates were then put back into vacuum for further coating.

Magnesium and silver were co-deposited at a rate of 2 Å/s. The ratio of Mg:Ag was 9:1. The thickness of this layer was 500 Å. Finally, 1000 Å Ag was deposited at the rate of 2.7 Å/s.

Characteristics of the Devices

Figure 3:
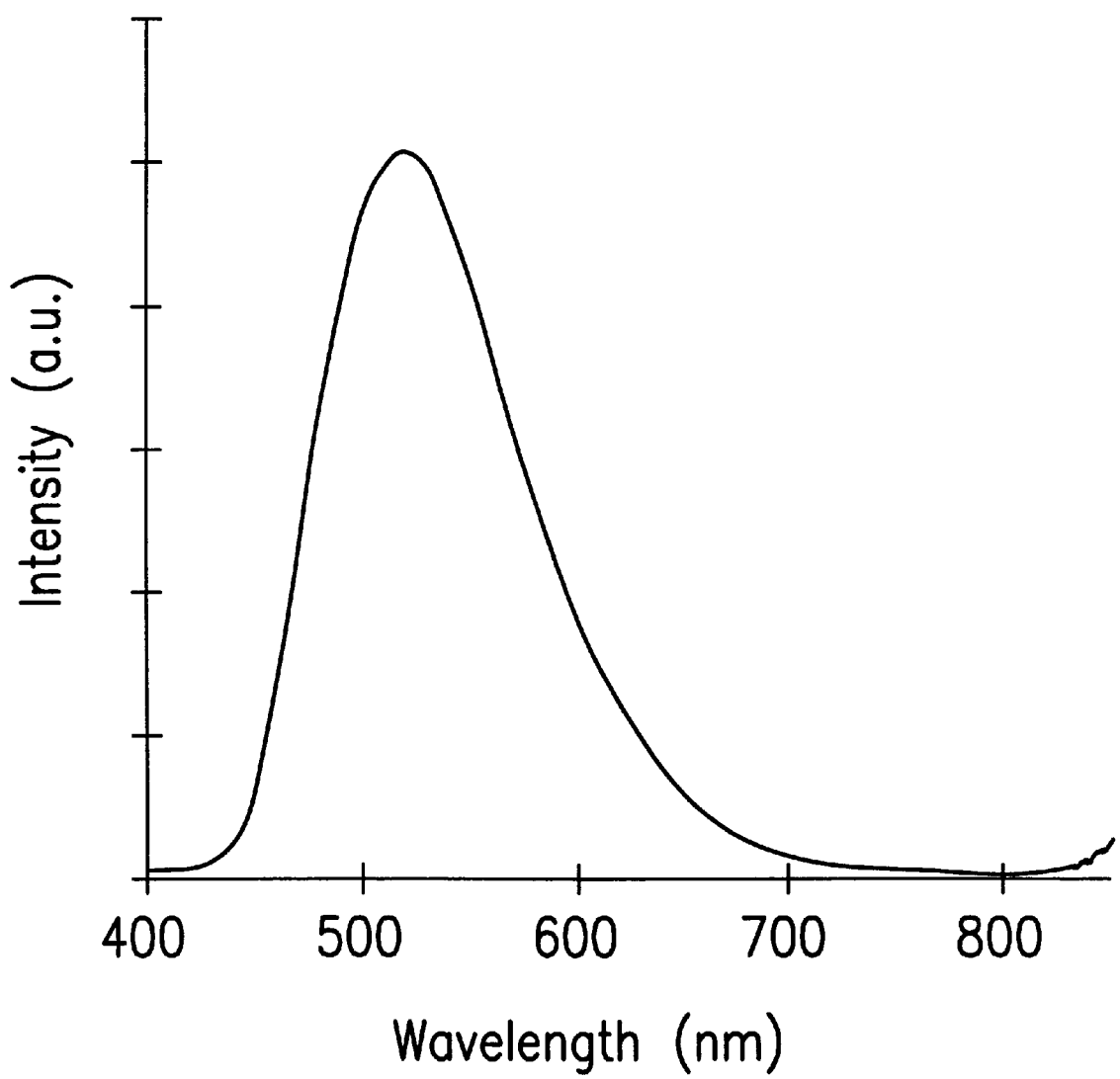
FIG. 3 shows the electroluminescent spectrum of the OLED prepared in the Example.
Figure 4:
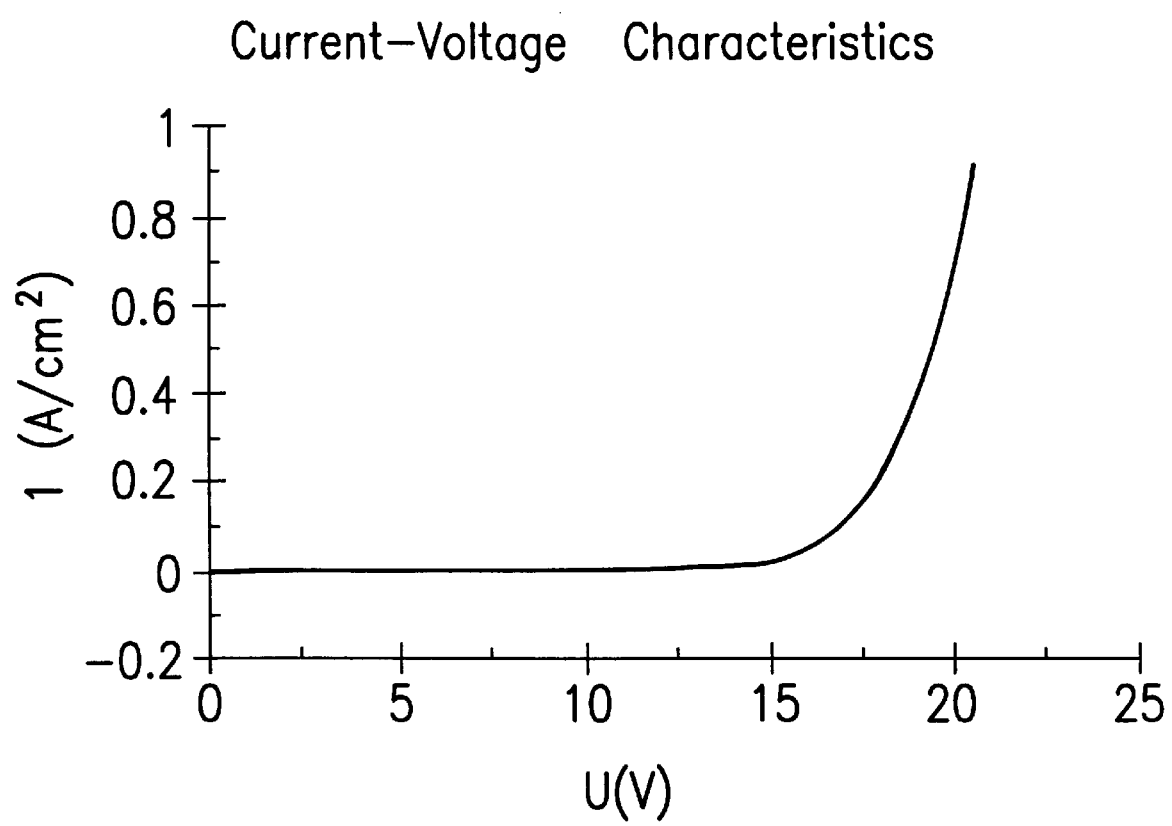
FIG. 4 shows the current-voltage (I–V) characteristics of the OLED prepared in the Example.

The devices were characterized within three hours of fabrication. Electroluminescent spectra, I–V curves, and quantum yields from direct front were measured. The electroluminescent spectrum for the device is shown in FIG. 3 and the current-voltage (I–V) characteristics are shown in FIG. 4. The external quantum yield was measured to be substantially identical to that of a standard Alq$_3$/TPD device made at the same time under substantially the same conditions. These results show that this class of asymmetric compounds can function as hole transporting materials in OLEDs.

What is claimed is:

1. A device for producing electroluminescence comprising a charge carrying layer having a glass structure, said charge carrying layer comprising a compound having a chemical structure as represented by a formula selected from the group consisting of:

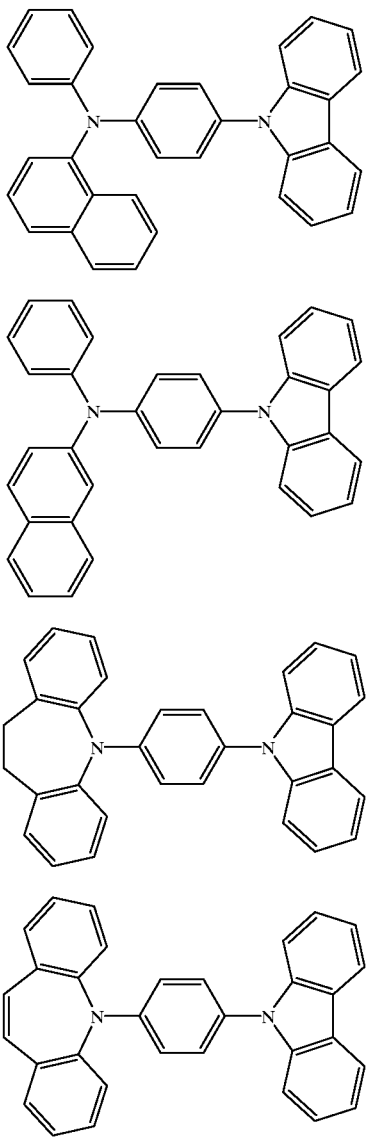

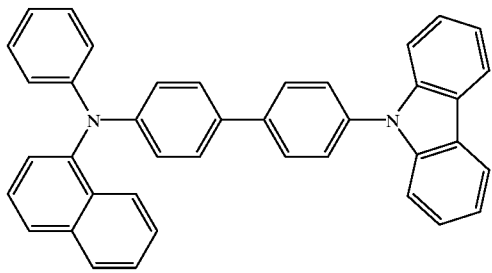

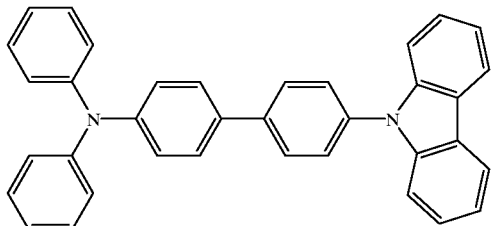

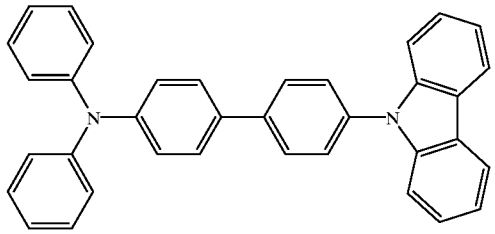

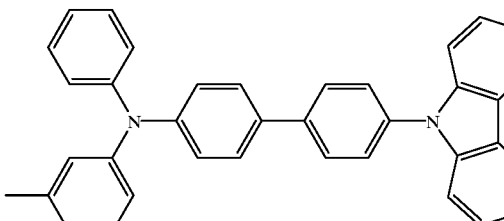

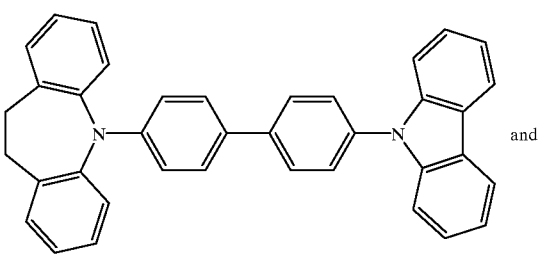

and

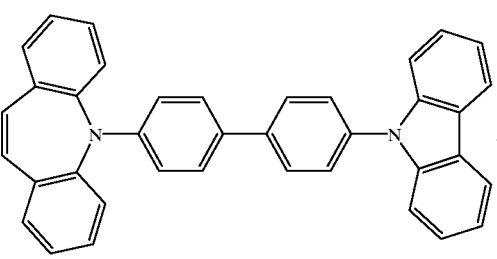

2. The device of claim 1 wherein said compound has the chemical structure as represented by the formula

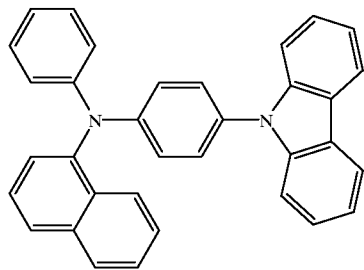

3. The device of claim 1 wherein said compound has the chemical structure as represented by the formula

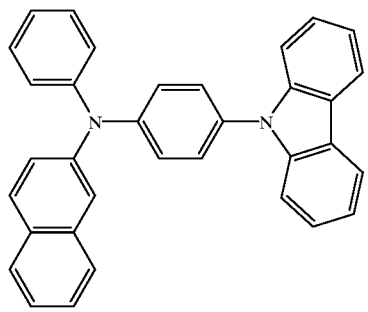

4. The device of claim 1 wherein said compound has the chemical structure as represented by the formula

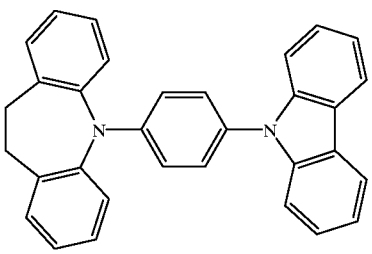

5. The device of claim 1 wherein said compound has the chemical structure as represented by the formula

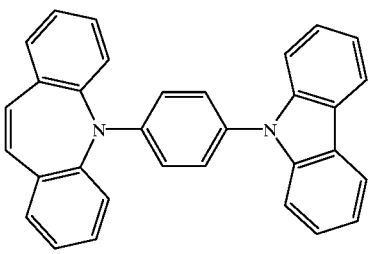

6. The device of claim 1 wherein said compound has the chemical structure as represented by the formula

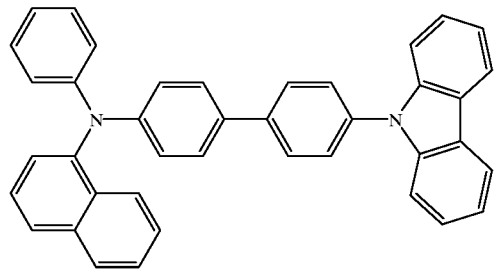

7. The device of claim 1 wherein said compound has the chemical structure as represented by the formula

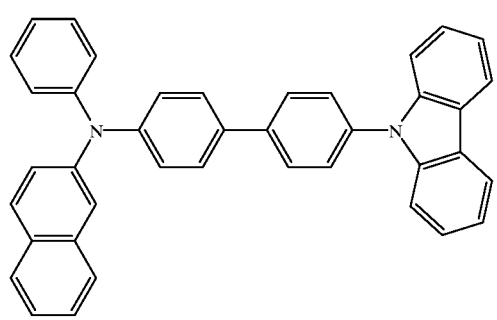

8. The device of claim 1 wherein said compound has the chemical structure as represented by the formula

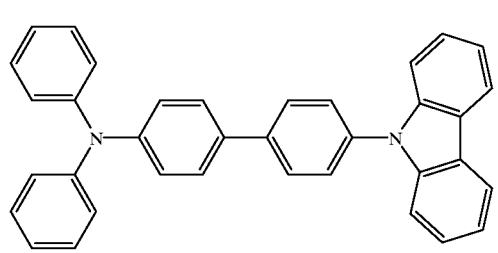

9. The device of claim 1 wherein said compound has the chemical structure as represented by the formula

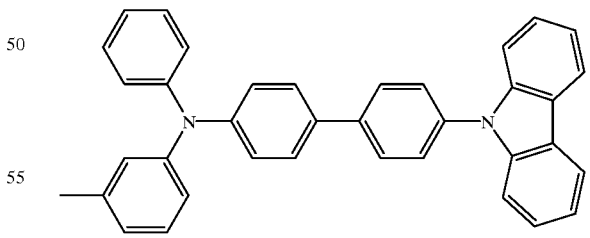

10. The device of claim 1 wherein said compound has the chemical structure as represented by the formula

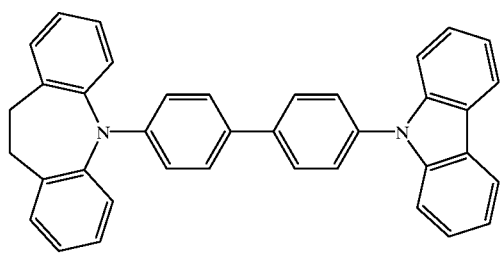

11. The device of claim 1 wherein said compound has the chemical structure as represented by the formula

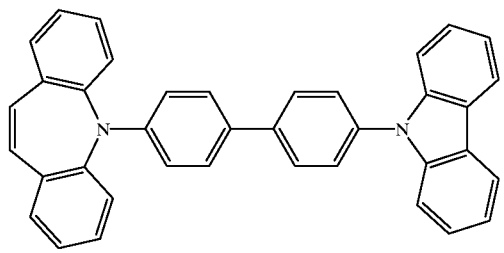

12. A device for producing electroluminescence comprising a charge carrying layer having a glass structure, said charge carrying layer comprising a compound having a chemical structure as represented by the formula

wherein $R_1$ represents

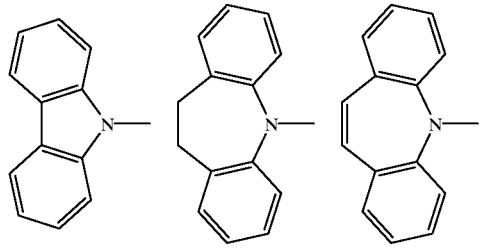

and $R_4$ represents

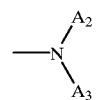

wherein $A_2$ and $A_3$ are phenyl, tolyl, or naphthyl.

13. A device for producing electroluminescence comprising a charge carrying layer having a glass structure, said charge carrying layer comprising a compound having a chemical structure as represented by the formula

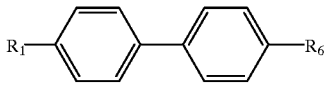

wherein $R_1$ represents

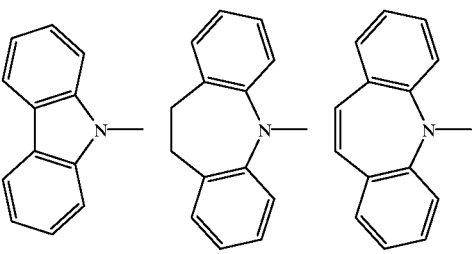

and $R_6$ represents

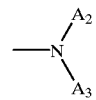

wherein $A_2$ and $A_3$ are phenyl, tolyl, or naphthyl.

\* \* \* \* \*